(12) United States Patent
Schade

(10) Patent No.: US 9,068,926 B2
(45) Date of Patent: Jun. 30, 2015

(54) PHOTO-ACOUSTIC GAS SENSOR AND METHOD FOR THE PRODUCTION AND USE THEREOF

(75) Inventor: Wolfgang Schade, Goslar (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 353 days.

(21) Appl. No.: 13/501,779

(22) PCT Filed: Oct. 7, 2010

(86) PCT No.: PCT/EP2010/064963
§ 371 (c)(1),
(2), (4) Date: Jun. 22, 2012

(87) PCT Pub. No.: WO2011/045221
PCT Pub. Date: Apr. 21, 2011

(65) Prior Publication Data
US 2012/0260719 A1   Oct. 18, 2012

(30) Foreign Application Priority Data
Oct. 15, 2009   (DE) .......................... 10 2009 045 724

(51) Int. Cl.
*G01N 21/17*   (2006.01)
*H05K 13/00*   (2006.01)

(52) U.S. Cl.
CPC ............. *G01N 21/1702* (2013.01); *Y10T 29/41* (2015.01); *G01N 2021/1704* (2013.01)

(58) Field of Classification Search
USPC ............... 73/24.01, 24.02, 579; 356/432, 502
See application file for complete search history.

(56) References Cited

U.S. PATENT DOCUMENTS

| | | | |
|---|---|---|---|
| 5,502,781 A * | 3/1996 | Li et al. .............................. | 385/4 |
| 5,559,358 A * | 9/1996 | Burns et al. .................... | 257/431 |
| 6,082,178 A | 7/2000 | Bernstein et al. | |
| 6,161,426 A | 12/2000 | Byatt et al. | |
| 7,304,732 B1 * | 12/2007 | Polcawich et al. ............ | 356/246 |
| 7,463,364 B2 * | 12/2008 | Yacoubian .................... | 356/502 |

(Continued)

FOREIGN PATENT DOCUMENTS

| CH | 686 589 A5 | 4/1996 |
|---|---|---|
| DE | 197 44 500 A1 | 4/1999 |

(Continued)

OTHER PUBLICATIONS

Stephen et al., Ultra-compact, high efficiency, quartz-enhanced photoacoustic spectroscopy based trace gas sensor platform. Oct. 2006 IEEE.*

(Continued)

*Primary Examiner* — Hezron E Williams
*Assistant Examiner* — Xin Zhong
(74) *Attorney, Agent, or Firm* — Brinks Gilson & Lione

(57) ABSTRACT

A photo-acoustic gas sensor and methods for producing same, the gas sensor having a resonance body and a device for detecting a vibration of the resonance body, including a device for optically detecting the location of at least one partial surface of the resonance body, wherein the resonance body and the device for detecting a vibration are disposed on exactly one substrate, the resonance body is formed by at least one first recess of the substrate, and the substrate is a semiconductor material.

12 Claims, 4 Drawing Sheets

(56) References Cited

U.S. PATENT DOCUMENTS

| | | | |
|---|---|---|---|
| 8,040,516 B2* | 10/2011 | Van Kesteren et al. | 356/432 |
| 2005/0117155 A1* | 6/2005 | Kosterev | 356/432 |
| 2010/0011836 A1* | 1/2010 | Kalkman et al. | 73/24.02 |
| 2011/0290002 A1 | 12/2011 | Heidrich et al. | |
| 2012/0151995 A1 | 6/2012 | Schade et al. | |

FOREIGN PATENT DOCUMENTS

| | | |
|---|---|---|
| DE | 696 10 225 T2 | 1/2001 |
| DE | 10 2008 047 658 B3 | 1/2010 |
| DE | 10 2009 029 002 B3 | 1/2011 |
| JP | 5172738 A | 7/1993 |
| WO | WO 03/104767 A2 | 12/2003 |
| WO | WO 2006/001842 A2 | 1/2006 |
| WO | WO 2006/092751 A1 | 9/2006 |
| WO | WO 2010/028865 A1 | 3/2010 |
| WO | WO 2011/023695 A1 | 3/2011 |

OTHER PUBLICATIONS

Sievila, P. et al., Fabrication and Characterization of an Ultrasensitive Acousto-Optical Cantilever; Ultrasensitive Acousto-Optical Cantilever, 2007, pp. 852-859, vol. 17, No. 5, IOP Publishing, Bristol, GB.

So, Stephen G., et al., Ultra-Compact, High Efficiency, Quartz-Enhanced Photoacoustic Spectroscopy Based Trace Gas Sensor Platform, 2006, pp. 292-293, IEEE.

Kosterev, A. A. et al., Quartz-enhanced Photoacoustic Spectroscopy, 2002, pp. 1902-1904, Optical Society of America.

Koskinen, V. et al., Cantilever Enhanced Photoacoustic Detection of Carbon Dioxide Using a Tunable Diode Laser Source, Jan. 23, 2007, pp. 451-454, vol. 86, No. 3, Springer-Verlag.

Ulbers, G., Integriert-optische Sensoren für die Weg-, Kraft-und Brechungsindexmessung auf der Basis von Silizium (Integrated-optical Sensors for the Measurement of Displacement, Force and Refractive Index on the Basis of Silicon), Apr. 1991, pp. 146-151, vol. 58, No. 4, Technisches Messen TM, R. Oldenbourg Verlag, Munchen, Germany.

Pellegrino, Paul M. et al., Miniature Photoacoustic Chemical Sensor Using Microelectromechanical Structures, 2004, pp. 42-53, vol. 5416, SPIE, Bellingham, WA.

International Preliminary Report on Patentability, dated Jul. 12, 2012, pp. 1-9, International Application No. PCT/EP2010/064963, The International Bureau of WIPO, Switzerland.

A A Kosterev et al., Quartz photoacoustic spectroscopy, dated Nov. 1, 2002, pp. 1902-1904, Optics Letter, vol. 27, No. 21, Optical Society of America, Washington, DC.

C Shönenberger et al., A differential interferometer for force microscopy, dated Oct. 1989, pp. 3131-3134, Review of Scientific Instruments, vol. 60, No. 10, New York, US.

J Breguet et al., Photoacoustic detection of trace gases with an optical microphone, dated 1995, pp. 29-35, Sensors and Actuators A 48, Switzerland.

Robert D Grober et al., Fundamental limits to force detection using quartz tuning forks, dated Jul. 2000, pp. 2776-2780, Review of Scientific Instruments, vol. 27, No. 7, American Institute of Physics, Melville, New York.

Samara L Firebaugh et al, Miniaturization and Integration of Photoacoustic Detection with a Microfabricated Chemical Reactor System, dated Jun. 2001, pp. 232-237, Journal of Microelectromechanical Systems, vol. 10, No. 2, IEEE, New York, US.

* cited by examiner

PHOTO-ACOUSTIC GAS SENSOR AND METHOD FOR THE PRODUCTION AND USE THEREOF

FIELD OF THE INVENTION

The invention relates to a photo-acoustic gas sensor, comprising a resonance body at least partly delimiting a volume intended for receiving molecules to be detected, and a device for identifying an oscillation of the resonance body.

An apparatus of the type mentioned in the introduction is known from A. A. Kosterev et al.: Quartz-enhanced photo-acoustic spectroscopy, Optics Letters, Vol. 27, No. 21 (2002) 1902. Said document discloses the use of a forked quartz crystal as a highly sensitive microphone which can be used to detect pressure fluctuations in a gas phase. In accordance with the known method, the pressure fluctuations are generated by means of a laser diode which selectively excites the molecules of the gas phase by means of spectrally narrowband radiation. On account of the high quality factor of the forked quartz crystal used for detection, the photo-acoustic measurement can be carried out with high sensitivity. The exciting light source with associated control electronics and also the evaluation electronics are separate from the actual gas sensor.

This known method has the disadvantage, however that the choice of materials for producing micro-tuning forks is restricted to piezoelectric materials. Furthermore, a piezo-voltage which is often only a few nano- or picovolts is measured for signal detection. As a result, the measurement can easily be influenced by electrical interfering signals. Furthermore, the space requirement of the gas sensor is limited by the space requirement of the exciting light source with associated control electronics and also the evaluation electronics, such that a mobile application is not possible.

Accordingly, the object of the invention is to provide a method and an apparatus for gas analysis which allows measurement with greater reliability and has a compact design.

SUMMARY OF THE INVENTION

The object is achieved by means of a photo-acoustic gas sensor comprising a resonance body and a device for identifying an oscillation of the resonance body, which comprises a device for optically detecting the location of at least one partial area of the resonance body, wherein the resonance body and the device for identifying an oscillation are arranged on exactly one substrate, and the resonance body is formed by at least one first cutout of the substrate, wherein the substrate comprises a semiconductor material.

In some embodiments of the invention the substrate may comprise silicon. As a result, simple and cost-effective production of the gas sensor by means of known methods and apparatuses appertaining to microelectronics and micromechanics is possible.

In some embodiments of the invention the resonance body may have at least two elements which are arranged approximately parallel and each of which is fixed to a connecting element by a base point and projects freely at their end opposite to the base point, wherein a second cutout is formed between both elements and the first cutout is formed between the substrate and one element. As a result, the device for reading out the signal and the device for optically exciting the molecules to be examined are arranged in one plane, such that particularly simple integration into a substrate becomes possible.

In some embodiments of the invention the device for identifying an oscillation may comprise an interferometer comprising at least two optical waveguides which are guided parallel in a partial section, such that a crosstalk of the signals respectively guided in the optical waveguides is possible. Within the meaning of the present description, crosstalk is understood to be the mutual influencing of the two waveguides guided parallel such that a signal coupled into the first waveguide can also be detected in the second waveguide. In this case, the amplitude of the signals in both waveguides can be different. Such an interferometer can be introduced by dry and/or depth etching into the substrate. In a further embodiment of the invention, the interaction of short light pulses with the substrate can be utilized for writing waveguides into the substrate. The individual light pulses can have a pulse length of less than 200 fs. In this way, a waveguide can be arranged at a predeterminable depth within the substrate.

In some embodiments of the invention at least one device for generating light and/or a device for detecting light and/or a device for electronic signal processing and/or a device for energy supply may be integrated on the substrate. Accordingly, the at least one device can be a photodiode, a light emitting diode or a laser diode. Furthermore, the at least one component can be a signal amplifier, an A/D converter, a discriminator, a transmitting device for a data signal or a receiving device for a data signal. Furthermore, the at least one device can comprise a capacitor or a solar cell for supplying further devices with power.

A device for generating light and/or a device for detecting light and/or a device for electronic signal processing and/or a device for energy supply can comprise a plurality of different electronic components, such as capacitors, resistors, inductances, diodes, transistors, microcontrollers, microprocessors, memory devices and further components not explicitly mentioned.

In some embodiments of the invention at least one electronic component may be manufactured by means of CMOS technology on the substrate. This allows the production of electronic, optical and micromechanical components in the same process.

In some embodiments of the invention at least one electronic component may be connected to the substrate by means of flip-chip bonding. As a result, it is possible to integrate components on the substrate which comprise at least one semiconductor material which differs from the semiconductor material of the substrate.

In some embodiments of the invention the gas sensor may comprise further at least one resonator which at least partly delimits a volume intended for receiving molecules to be detected. As a result, the sensitivity of detection is increased and the structural size of the gas sensor is reduced.

In some embodiments of the invention the resonator may be connected to the substrate by means of a bonding method or may be monolithically integrated in the substrate. In this way, the number and/or the size of the resonators can be varied within wide limits.

In some embodiments of the invention the resonator may have a rectangular cross section. The cross section may have a length and/or width of approximately 100 µm to approximately 1000 µm. The longitudinal extent of the resonator may be approximately 1 mm up to approximately 10 mm. The dimensions may be coordinated with the wavelength of a standing wave that forms. As a result, the coupling of the photo-acoustically induced wave to the resonance body used for detection can be improved.

In some embodiments of the invention at least one hole may be made in the boundary wall of the resonator. Such a hole may have a diameter of approximately 10 µm to approximately 1000 µm.

In some embodiments of the invention the gas sensor may comprise at least one contact layer via which at least two electronic components are electrically connected. The contact layer may comprise a metal or an alloy or a semiconductor material provided with a dopant. A plurality of contact layers may be separated by at least one layer comprising an insulator or a semiconductor material not provided with a dopant.

In some embodiments of the invention the gas sensor may comprise at least one optical waveguide which is integrated using silicon-on-insulator technology (SOI) on and/or inside the substrate.

Furthermore, the object is achieved by means of a method for photo-acoustically detecting molecules in the gas phase, comprising the following steps: introducing the molecules to be detected into a volume at least partly delimited by at least one micromechanical resonator, supplying light for exciting a photo-acoustic signal into the volume intended for receiving the molecules to be detected, identifying an oscillation of a resonance body by optically detecting the location of at least two partial areas of the resonance body and transmitting a signal representing the oscillation of the resonance body by means of a radio signal.

In some embodiments of the invention the radio signal may comprise a WLAN signal and/or a Bluetooth signal. As a result, the gas sensor can be connected to a device for data processing or to a device for data transmission. To provide transmission over greater distances, for example via a LAN, a WAN or a mobile radio network.

In some embodiments of the invention a standing acoustic wave may be formed in the resonator as a result of the incident light. This results in an amplification of the photo-acoustic signal.

In some embodiments of the invention energy may be supplied by means of at least one solar cell to at least one device for supplying light and/or at least one device for identifying the oscillation of the resonance body and/or at least one device for transmitting a signal representing the oscillation of the resonance body. This enables autonomous and maintenance-free operation of the gas sensor.

In some embodiments of the invention the solar cell ambient light may be incident on the solar cell at least during operation of the gas sensor.

In some embodiments of the invention the solar cell may be irradiated with an artificial light source at least during operation of the gas sensor. In this case, provision can be made for switching the gas sensor on and off by switching the artificial light source on and off at a predetermined time.

In some embodiments of the invention the artificial light source may be part of a luminaire used for the general lighting of a room.

In some embodiments of the invention the gas sensor may comprise at least one capacitor. As a result, electrical energy may be be stored to ensure the energy supply of the gas sensor even when no light is incident on the gas sensor.

Furthermore, the object is achieved by means of a method for producing a gas sensor, comprising the following steps: providing a substrate comprising a semiconductor material, producing at least one electronic component for generating light and/or for detecting light and/or for electronic signal processing and/or for energy supply on the substrate, introducing at least one first cutout and/or a second cutout into the substrate.

In some embodiments of the invention introducing at least one first cutout and/or a second cutout into the substrate may be effected by means of an etching method. This can be a dry-chemical etching step.

In some embodiments of the invention the method furthermore may comprise the step of producing a resonator at least partly delimiting a volume intended for receiving molecules to be detected.

In some embodiments of the invention the resonator may be connected to the substrate by means of bonding.

In some embodiments of the invention the resonator may be produced monolithically on the substrate.

In some embodiments of the invention at least one component may be produced using CMOS technology on the substrate.

In some embodiments of the invention at least one component is connected to the substrate by means of flip-chip bonding.

In some embodiments of the invention the gas sensor according to the invention is used for process control in industrial installations or heating installations.

In some embodiments of the invention the gas sensor according to the invention is used for room air monitoring. In one embodiment, a measurement of the ratio of $CO_2$ and/or $H_2O$ in the room air may be carried out. The output signal of the gas sensor may be used for controlling a ventilation or air-conditioning system.

In some embodiments of the invention the gas sensor according to the invention may be used for breath gas monitoring. This can comprise determining the $CO_2$ and/or $O_2$ and/or acetone and/or alcohol content. Accordingly, with the gas sensor it is possible to carry out a breath alcohol measurement or to identify acetonemia or to regulate a respirator/ventilator.

In some embodiments of the invention the gas sensor according to the invention may be adapted for detecting gas emanations via the skin of a living organism. This may comprise determining the acetone content. Accordingly, the gas sensor may be used to identify acetonemia, such that the gas sensor can be used for treatment control in diabetes.

In some embodiments of the invention the gas sensor according to the invention may be used for determining the composition of a fuel gas, thereby monitoring the calorific value of a fuel gas having a changing composition, for example the calorific value of a biogas from a biogas installation. This allows the open-loop or closed-loop control of the energy conversion of an internal combustion engine being operated with said fuel gas.

In some embodiments of the invention the gas sensor according to the invention may be used for fire protection monitoring. For this purpose, provision can be made for detecting the content of $CO_x$ and/or $NO_x$ in the room air.

In some embodiments of the invention the gas sensor according to the invention may be used for monitoring foodstuffs, such as fruit and vegetables, for example, and plants in refrigerated containers. Provision may be made for detecting the content of ethene ($C_2H_4$), $CO_2$, $H_2O$, $O_2$ and/or $N_2$ in the ambient air. In some embodiments, the sensor signal may be used as an input signal of an open-loop control and/or closed-loop control used to control the energy of at least one refrigerating unit. In this way, it is possible to reduce the energy consumption and $CO_2$ emission of the refrigerating unit.

SHORT DESCRIPTION OF THE DRAWINGS

DETAILED DESCRIPTION

Figure 1:
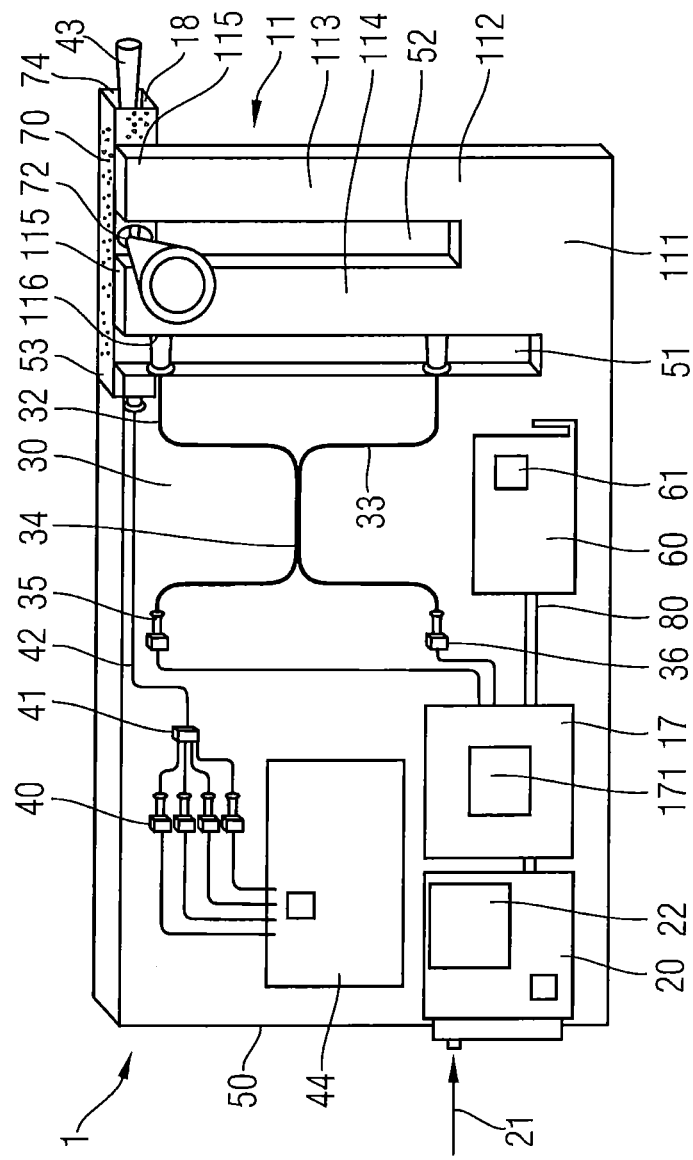
FIG. 1 shows a gas sensor according to the invention in accordance with a first embodiment of the invention.

FIG. 1 shows a photo-acoustic gas sensor 1 in accordance with one embodiment of the present invention. The gas sensor 1 is provided for detecting the presence and/or the quantity of one or more molecular species in a gas phase to be examined which is supplied to the gas sensor 1.

The gas sensor 1 comprises a substrate 50. The substrate 50 can comprise silicon. The silicon can be provided with a dopant, for example boron, aluminum, gallium, nitrogen, phosphorus or arsenic, for setting a predeterminable electrical conductivity. The substrate can be a monocrystalline substrate. The substrate can have a thickness of approximately 0.1 mm to approximately 1 mm. The surface of the substrate can be provided with an insulating dielectric, for example an oxide, a nitride or an oxinitride.

In order to detect photo-acoustically induced oscillations, the gas sensor 1 comprises a resonance body 11. In the embodiment illustrated, the resonance body 11 comprises at least two elongate elements 113 and 114 arranged approximately parallel. Each of the elements 113, 114 is fixed to a connecting element 111 by its base point 112. In some embodiments of the invention, the end 115 opposite to the base point 112 can project freely. In other embodiments of the invention, the end 115 can be in contact with a resonator 70 or serve for fixing the resonator 70 to the substrate 50.

In some embodiments, the elements 113 and 114 arranged parallel can be formed by introducing a first cutout 51 and a second cutout 52 into the substrate 50. In this case, the elements 113 and 114 and also the connecting element 111 and the substrate 50 can be embodied integrally. The cutouts 51 and 52 can be obtained by wet- or dry-chemical etching. For this purpose, partial areas of the substrate 50 can be protected against the corrosive attack of the etchant by a mask. A photoresist or a hard mask can be used for this purpose. In other embodiments of the invention, the cutouts 51 and 52 can be produced by machining, for example by micro-grinding or micro-milling. In yet another embodiment, the cutouts 51 and 52 can be produced by laser material processing, for example by laser ablation or by exposure and etching of the substrate 30. For this purpose, it is possible to use a pulsed laser having, in some embodiments, a pulse duration of less than 200 fs.

For photo-acoustically detecting molecules in the gas phase to be examined, the gas sensor 1 proposed has at least one resonator 70. The resonator 70 comprises a hollow body, for example in the form of a cylinder or a prism. FIG. 1 illustrates a parallelepipedal hollow body. The resonator can have a longitudinal extent of approximately 1 mm to approximately 10 mm. The edge length or the diameter of the end face 74 can be approximately 1 µm to approximately 500 µm. If the end face 74 is rectangular, both edges can have an identical edge length or else a different edge length.

The lateral surface of the resonator 70 can have a plurality of holes 73 in order to enable the access of the gas phase to be examined into the interior 18 or in order at least to accelerate the gas exchange between the interior 18 of the resonator 70 and the exterior.

The resonator 70 can be produced from the material of the substrate 50 and can be monolithically integrated into the gas sensor 1. In other embodiments of the invention, the resonator 70 can be produced from a separate substrate in a dedicated production process, for example by means of etching or laser aberration, and can be bonded at a predetermined location of the substrate 50. In this way, a material whose chemical resistance and/or processability is optimized for the respective purpose of use can be chosen for the resonator 70. The bonding connection can be effected at an end face 53 of the substrate 50 facing the cutout 51. In other embodiments of the invention, the bonding connection can also be effected at the end 115 of one of the elements 113 or 114 arranged approximately parallel.

During operation of the gas sensor 1, light having at least one predeterminable wavelength and/or pulse shape is radiated into the resonator 70. In this case, the wavelength is coordinated with the energy difference between the ground state and at least one excited state of the molecule to be detected, such that a resonant absorption of the light radiated in is made possible. Depending on the molecular species to be detected and the transition chosen, the light can have a wavelength of approximately 3 µm to approximately 15 nm. In some of the embodiments of the invention, the wavelength can be chosen between approximately 0.8 µm and approximately 3 µm.

The light absorption by the gas phase to be examined in the resonator 70 can induce a standing acoustic wave in the interior of the resonator 70. The length of the resonator 70 can be selected such that the maximum intensity of the standing acoustic wave lies in the center of the longitudinal extent of the resonator. At this location, at least one opening 72 can be arranged through which at least part of the sound energy escapes. As can be seen in FIG. 1, the opening 72 joins the second cutout 52, such that the acoustic wave can couple to the elongate elements 113 and/or 114.

As a result of the action of the acoustic wave generated in the resonator 70, at least one of the elongate elements 113 or 114 is caused to oscillate. In this case, the amplitude of this oscillation varies with the intensity of the acting sound wave, which is in turn dependent on the concentration of the absorbent molecules in the interior 18 of the resonator 70. In this way, the amplitude of the oscillation of the element 114 and/or 113 is a measure of the concentration of the molecules to be detected in the gas phase to be examined.

The oscillation of the resonance body 11 is read by means of an interferometer 30. In the embodiment illustrated, the interferometer 30 comprises at least two optical waveguides 32 and 33 which are guided parallel in a partial section 34, such that a crosstalk of the signals respectively guided in the optical waveguides 32 and 33 is possible. The crosstalk of the signals in the partial section 34 leads to an evanescent coupling of the signals guided in the waveguides 32 and 33.

In order to detect the oscillation of the resonator 11, an interrogating light signal is generated by means of a coherent light source 35, for example a laser diode, and coupled into the waveguide 32. As a result of the evanescent coupling of the waveguides, the light from the light source 35 emerges from both orifices of the optical waveguides 32 and 33 into the cutout 51. The light is subsequently reflected at two partial areas 116 of the element 114. The reflected light is at least partly coupled into the waveguides 32 and 33. On account of the different distance from the connecting element 111, both partial areas oscillate with a different amplitude such that the light reflected at the respective partial areas 116 experiences a path difference or phase shift. As a result of the evanescent coupling of the two reflective light signals in the partial section 34 of the optical waveguides 32 and 33, said phase shift is imaged into an interference pattern, which is detected by a detector 36, for example a photodiode.

A device 17 is available for driving the coherent light source 35 and for conditioning the signals of the detector 36. The device 17 comprises at least one electronic component 171, for example a resistor, a capacitor, an inductance, a diode, a transistor, or a more complex component composed of a plurality of components, such as a microprocessor, a microcontroller, an amplifier, a discriminator, an A/D converter or a memory.

The signal of the detector 36 received by the device 17, after it has been processed in the device 17, can be passed on via an electrical or optical data connection 80 to the device 60. The device 60 can also comprise at least one of the above-mentioned components in order to digitize store or transmit the received signals. For this purpose, the device 60 can be designed to store the data in a nonvolatile memory, for example a flash memory. Alternatively or cumulatively the device 60 can be designed to transmit the received data by means of a radio interface 61. By way of example, the radio interface 61 can operate according to the Bluetooth standard known per se or according to the WLAN standard. The radio interface 61 can transmit the data in this way to a data processing device, for example a computer, where they can be further evaluated and/or visualized and/or stored. In other embodiments of the invention, the data can be transmitted by means of the radio interface 61 to a device for data transmission, which transmits the data to a more remote data processing device. The device for data transmission can comprise a cellular telephone, for example.

The light required for generating the photo-acoustic signal is generated by means of at least one light source 40. The light source 40 can generate coherent light. The light source 40 can be designed to emit light having different wavelengths or the light source 40 can be a light source that is tunable between an upper and a lower limiting frequency. In some embodiments of the invention, a multiplicity of light sources 40 can be present, as a result of which either the intensity of the emitted light can be increased or a plurality of different wavelengths can be provided for exciting different molecules by means of respectively assigned light sources. FIG. 1 illustrates four light sources, which can be integrated for example in the form of light emitting diodes or diode lasers on the substrate 50.

The light from the light sources 40 is guided by means of assigned waveguides to a multiplexer 41, which is likewise arranged on the substrate 50. The waveguide 42 proceeds from the multiplexer 41, which waveguide opens at the end face 53 of the substrate 50. Since the resonator 70 opens with its narrow side likewise at the end face 53, the light can emerge from the waveguide 42 and enter the resonator 70. The free beam 43 then radiates through the resonator 70, wherein the light as already described above excites a photo-acoustic signal in the interior 18 of the resonator 70.

One advantage of the arrangement described in FIG. 1 of the previously known gas sensors is that the reading of the photo-acoustically induced oscillation of the resonance body 11 and the optical excitation of the photo-acoustic signal in the resonator 70 are effected in one plane. As a result, simple production by means of conventional etching technologies, and the cost-effective manufacture of large numbers on a single wafer are possible.

Furthermore, the gas sensor 1 has driving electronics 44 that generate electrical control signals for the light sources 40. The electrical control signals can provide, for example, for the light sources 40 to be driven cyclically in order to cyclically emit a plurality of different wavelengths and, in this way, to cyclically detect a plurality of different molecules. A tunable light source 40 can be varied in terms of the wavelength by means of electrical signals from the device 44. Furthermore, the device 44 can provide the required stabilized operating currents and/or voltages for the operation of the light sources 40.

Furthermore, the device 44 can be used to operate the light sources 40 in pulsed fashion. In some environments, the pulse frequency can correspond approximately to the resonant frequency of the resonance body 11. In this way, the photo-acoustic signal can be measured with particularly little background or no noise by means of a lock-in amplifier. Such a lock-in amplifier can be integrated, for example, in the device 17 for signal processing and/or in the device 44 for driving the coherent light sources 40.

Furthermore, the device 44 can be provided for initiating measurements at predeterminable time intervals, such that continuous monitoring of the gas atmosphere surrounding the gas sensor is effected with a specific predeterminable temporal resolution.

A device 20 for energy supply is available for supplying the device 44, the device 17, the device 60 and also the light sources 35 and 40 with power. The device 20 can comprise at least one solar cell 22 which generates the required electricity from ambient light or from light from an artificial light source supplied to the gas sensor 1 specifically for this purpose. The gas sensor 1 can then be switched on or off by the light source being switched on or off.

As a result of the integration of the solar cell 22, the gas sensor 1 is fully autonomous and can be used either as a discrete gas sensor element by itself or as part of further electrical or electronic devices. By way of example, the gas sensor 1 can be inserted into a luminaire for the general lighting of a room and in this way can monitor the room air while the luminaire is in operation or ambient light from a window opening is incident on the luminaire.

Furthermore, the device 20 can have one or a plurality of capacitors which ensure the electrical energy supply even when the solar cell 22 is shaded.

Furthermore, the device 20 can have an interface 21, via which, by means of a wired, a wireless or a fiber-optical connection, stored measurement data can be read out from the gas sensor 1 or a measuring program to be processed can be loaded into the device 44. In the case of a wired interface 21, the latter can also be used to supply electrical energy to the gas sensor 1. In this case, the solar cell 22 can also be omitted in some embodiments of the invention.

If the substrate 50 comprises a silicon substrate, the electronic components 22 and 171 of the devices 44, 20, 17 and 60 can be produced at least partly using CMOS technology directly on the substrate 30. A compact construction of the gas sensor 1 that is less sensitive to disturbances results in this way. Since both the micromechanical and the electronic and photonic components of the gas sensor 1 is effected in a manner known per se using known techniques of semiconductor fabrication the gas sensor 1 can be provided cost-effectively in large numbers.

For electrically connecting the different electronic devices 17, 20, 44 and 60 and also the light sources 35 and 40 and the detector 36 at least one metallization plane can be provided which can be applied to the substrate 50 in a manner known per se and patterned by means of a photoresist.

The waveguides 32, 33 and 42 can be embodied, for example, as ridge waveguides or as planar waveguides. In this way, it is also possible to integrate the waveguides using established methods of semiconductor technology on the substrate 50. In some embodiments, it is also possible to use laser pulses for writing the waveguides into the substrate.

In some embodiments of the invention, the photonic components such as the light sources 40 and 35 and also the detector 36 can also comprise a different semiconductor material than the substrate 50, for example a group III nitride or gallium arsenide. The photonic components can be constructed from a plurality of different layers in the form of a quantum well structure or a superlatice. The photonic components can be deposited heteroepitaxially on the substrate 50 or can be applied to the substrate 50 comparatively simply by means of upside down flip-chip bonding.

As a result of the complete integration of the micromechanical sensor elements 11 and 70, the fiber-optic sensor system, the light sources 40 and 35, the signal processing 17 and 60 and the power supply 20 onto a single semiconductor substrate 50, it is possible to provide a compact gas sensor 1 which is fully autonomous during operation and which is suitable for mobile and maintenance-free operation. The sensor can also be used at inaccessible locations and/or in harsh ambient conditions.

Figure 2:
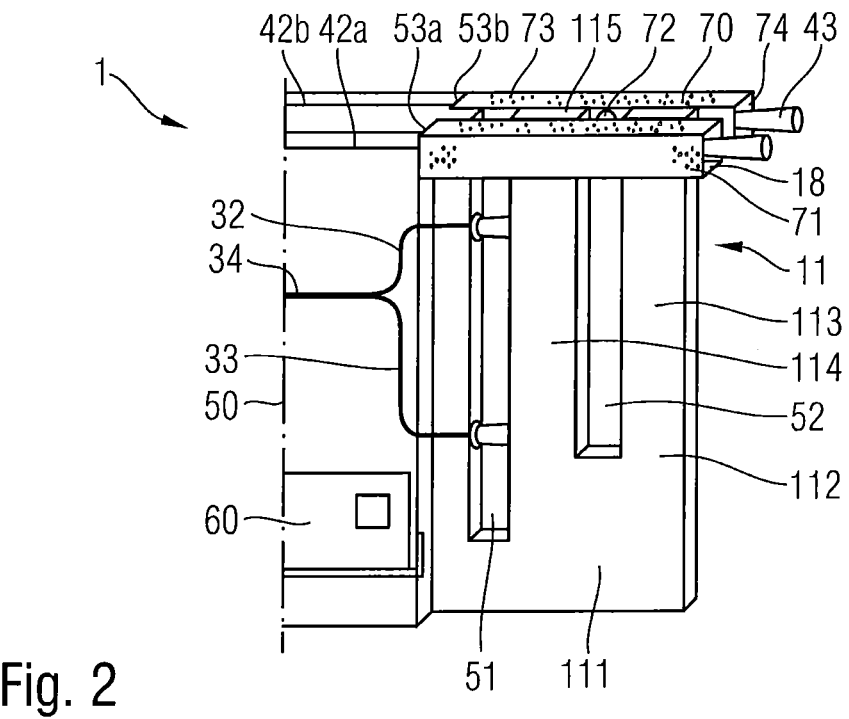
FIG. 2 shows a detail of a second embodiment of the gas sensor according to the invention.

FIG. 2 shows an alternative embodiment of the gas sensor 1. Since the differences with respect to the embodiment in accordance with FIG. 1 are restricted to the region of the resonator 70, the gas sensor is not illustrated completely in FIG. 2, rather only the region of the resonance body 11 and of the resonator 70 is illustrated.

The gas sensor 1 in accordance with FIG. 2 likewise comprises a substrate 50, on which waveguides 32, 33, 42a and 42b are integrated, as described in association with FIG. 1. Furthermore, the gas sensor in accordance with FIG. 2 can have electronic components for signal generation, for signal processing, for data transmission and for electrical energy supply, as described in association with FIG. 1. FIG. 2 merely illustrates by way of example the device 60 for data processing.

The gas sensor 1 in accordance with FIG. 2 comprises a resonance body 11 for detecting photo-acoustic oscillations as described in association with FIG. 1. For reading the photoacoustically induced oscillation of the element 114 an interferometer 30 is once again available, which is formed from the waveguides 32 and 33 having an evanescent coupling in a partial section 34.

A first resonator 70 and a second resonator 71 are available for generating the photo-acoustically induced signal. One or both resonators can have a plurality of holes 73 which enable or at least support the gas exchange between the interior 18 of the resonators and the volume surrounding the resonators.

In the region of the resonance body 11, the material thickness of the substrate 50 is reduced on both sides, thus resulting in two end faces 53a and 53b on both sides relative to the resonance body 11. At said end faces 53a and 53b, the resonators 70 and 71 are respectively fixed by means of bonding.

During operation of the gas sensor 1, light 43 in the free beam radiates through each resonator 70 and 71, such that a standing acoustic wave can form in each resonator 70 and 71. Each of the resonators 70 and 71 has an assigned opening 72, through which at least part of the acoustic power of the standing wave can be coupled out into the second cutout 52. In this way, the optoacoustically induced signal can couple to the resonance body 11 and excite the later to form a detectable oscillation.

The light 43 is supplied to each of the resonators 70 and 71 by a respectively assigned waveguide 42a and 42b. The waveguides 42a and 42b run at different depths in the substrate 50, such that one of the waveguides opens at the end face 53a and the other waveguide opens at the end face 53b.

The waveguides 42a and 42b can in each case transport the light from a light source 40, such that the same molecular species is detected in both resonators 70 and 71. In this way, the acoustic signal coupled out from the openings 72 is amplified and the sensitivity of detection is increased. For this purpose, the intensity of a light source 40 can be divided between both waveguides 42a and 42b for example approximately half each. In another embodiment, each of the waveguides 42a and 42b can be assigned a dedicated light source in order to utilize the intensity of two light sources.

In another embodiment of the invention, provision can be made for transporting in each waveguide 42a and 42b the light from a respectively assigned light source 40 having a different wavelength. As a result, a different molecular species can be detected in each of the resonators 70 and 71, such that the presence of two different molecular species in the gas phase to be examined can be ascertained simultaneously. In yet another embodiment of the invention, the different wavelengths of the light transported in the optical waveguide 42a and 42b can be used to excite different optical transitions or rotation transitions or oscillation transitions of the same molecule, such that a molecular species is measured twice. In this way, the measurement results can be plausibilized and the sensitivity can be increased and/or the measurement error can be reduced.

Figure 3:
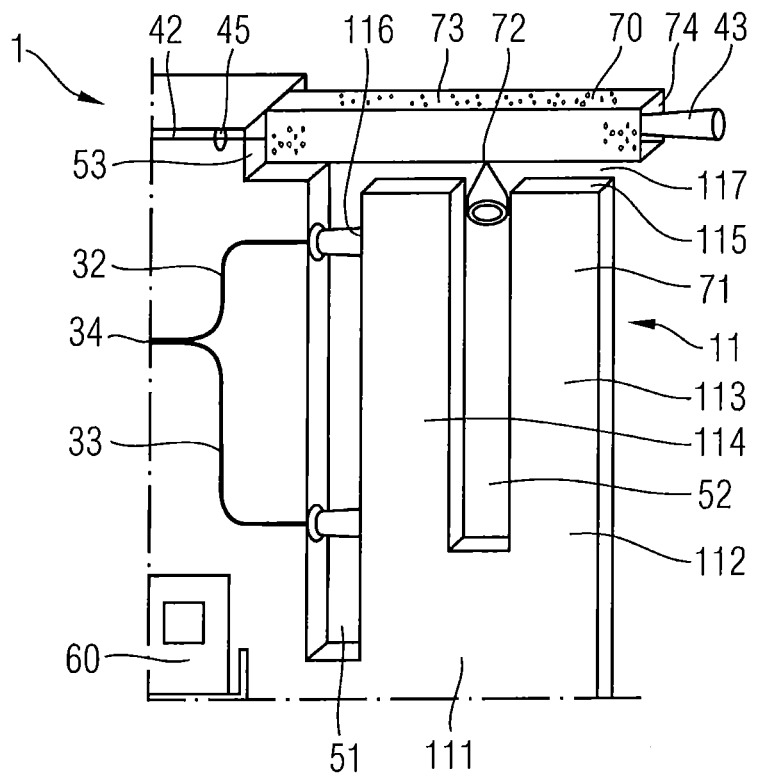
FIG. 3 shows a partial region of a gas sensor in accordance with a third embodiment of the invention.

FIG. 3 shows a further embodiment of the gas sensor proposed. FIG. 3, too, merely shows an excerpt from a gas sensor element, wherein the elements present without any changing in comparison with FIG. 1 are not illustrated.

The gas sensor in accordance with FIG. 3, too, comprises a substrate 50, on which electronic assemblies 60, waveguides 32 and 33 and photonic components can be arranged, as described in association with FIG. 1. The gas sensor in accordance with FIG. 3, too, comprises a resonance body 11, by means of which photo-acoustically induced signals can be amplified as described in association with FIGS. 1 and 2.

The resonator 70 again has an approximately rectangular end face 74. The lateral surface of the resonator 70 can again be equipped with holes 73 which facilitate or enable the gas exchange between the interior 18 of the resonator and the exterior thereof.

Since the resonator 70 is arranged above the resonance body 11, the hole 72 through which the photo-acoustically induced signal emerges from the resonator is situated at the underside of the resonator 70 facing the resonance body 11. In order to provide space for receiving the resonator at the end face 53, the elements 113 and 114 arranged approximately parallel are shortened at their end 115 opposite to the base point 112 right up to the surrounding substrate. The waveguide 42 via which the light provided for exciting the molecules in the gas phase to be examined is guided from the light sources 40 also opens at the end face 53.

The geometry illustrated in FIG. 3 is particularly suitable for monolithic integration of the resonator 70. For this purpose, the resonator 70 is produced from the material of the substrate 50, for example by etching or laser material processing or machining. Finally, the resonator 70 can be freed of the resonance body 11 by virtue of the gap 117 also being produced simultaneously or sequentially with the first cutout 51 and the second cutout 52, the resonator 70 being separated from the end 113 of the elongate elements 113 and 114 by said gap.

Figure 4:
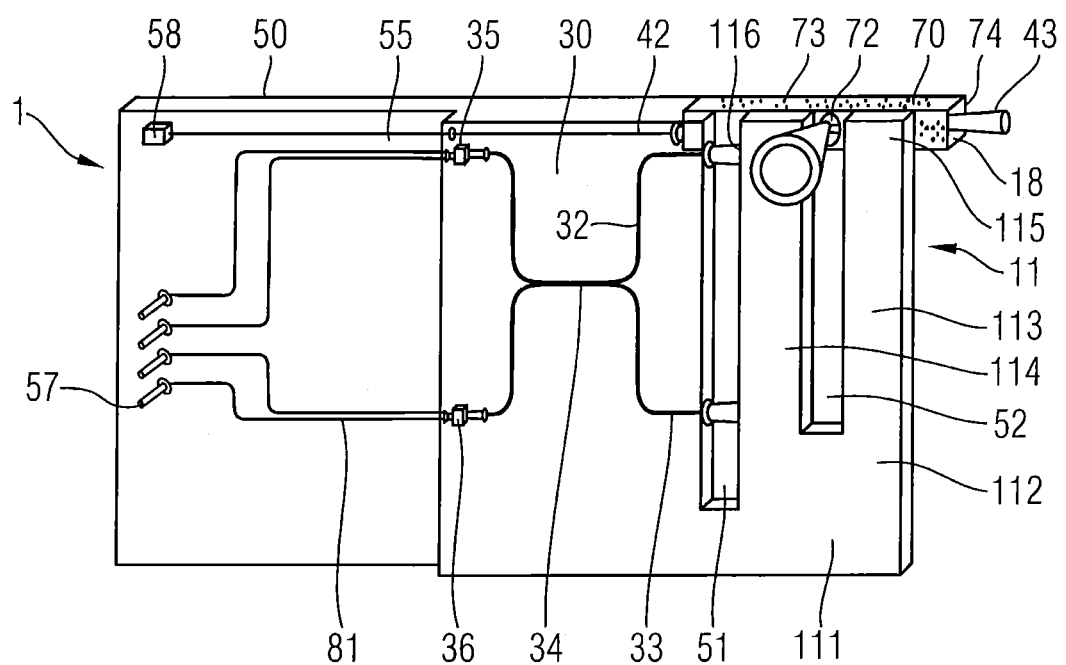
FIG. 4 shows a part of a gas sensor having a modular construction.
Figure 5:
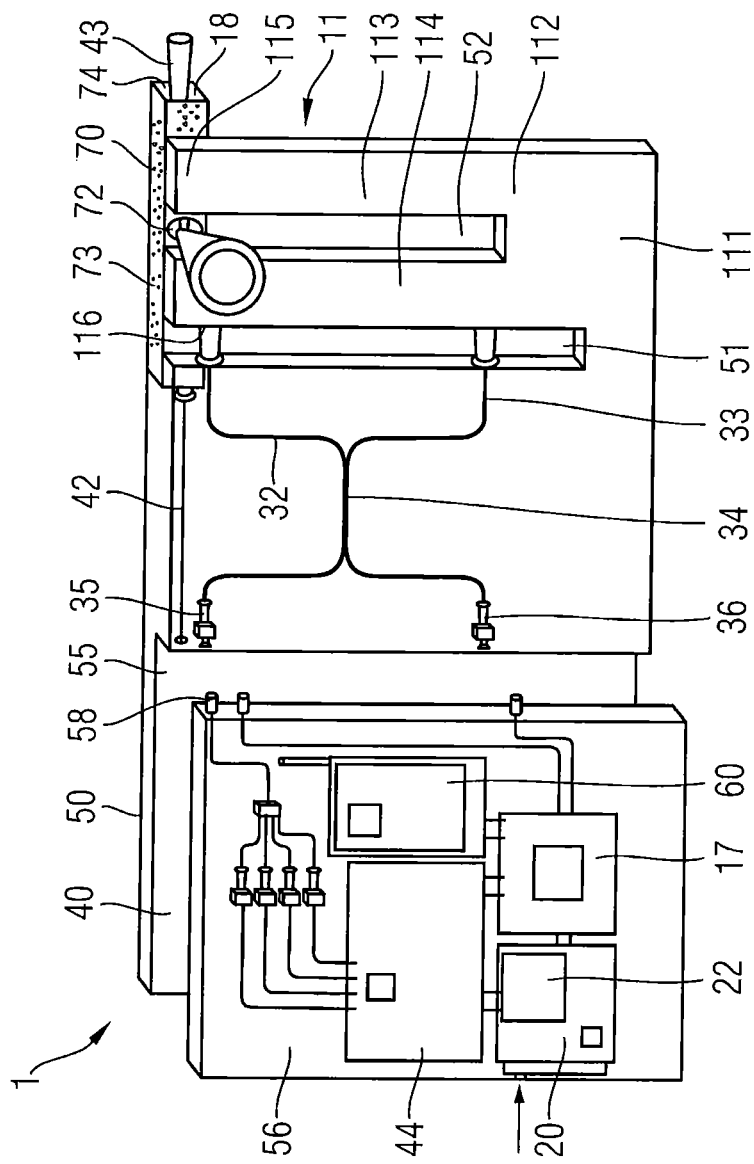
FIG. 5 shows an exploded drawing of the gas sensor having a modular constructions.

FIGS. 4 and 5 show a further embodiment of the proposed gas sensor having a modular construction.

FIG. 4 shows the first substrate 50. In the embodiment illustrated, the first substrate 50 comprises the resonance body 11 and a resonator 70. Although only one embodiment of the resonator 70 is illustrated in FIG. 4, all embodiments of the resonator 70 and of the resonance body 11 disclosed in association with FIGS. 4 and 5 can be used.

Furthermore, the first substrate 50 comprises at least one waveguide 42 which can be used for coupling an optical radiation for exciting a photo-acoustic oscillation in the interior 18 of the resonator 70. The waveguide 42 can be integrated by means of silicon-on-insulator technology into or onto the substrate 50, as described in association with FIG. 1.

Furthermore, the substrate 50 is provided with a micro-optically integrated interferometer 30. The interferometer 30 comprises a coherent light source 35. The radiation from said light source can be coupled into the waveguide 32, which has an evanescent coupling to the waveguide 33 by means of a partial section 34. After the reflection of the light emerging from the waveguides 32 and 33 at the partial areas 116 of the elongate element 114, it is possible to detect an oscillation of said element in the photodetector 36.

In the embodiment in accordance with FIG. 4 the substrate 50 comprises, apart from the photodetector 36 and the coherent light source 35, no electronic components such as, for example, the device 40 for generating light, the devices 44 and 60 for electronic signal processing or the device 20 for energy supply. These components of the gas sensor proposed are arranged on a second substrate 56 as explained in association with FIG. 5. In other embodiments of a modularly constructed gas sensor 1, the division of the components between the two substrates 50 and 56 can, of course, also be effected differently. Moreover, the invention does not teach the use of exactly two substrates as a solution principle.

Electrical connection contacts 57 are available for connecting the second substrate 56 to the first substrate 50 said connection contacts engaging into corresponding mating contacts of the second substrate 56. In this case, the number of four pin contacts illustrated in FIG. 4 should be seen merely by way of example. In other embodiments of the invention the number of contacts can be larger or smaller, depending on the magnitude the number of electronic and/or optoelectronic components integrated on the substrate 50. Furthermore, pin contacts, socket contacts or planar contact elements can be used. The invention does not disclose the use of exactly four pin contacts as a solution principle.

Electrical lines 81 are available for electrically connecting the contact elements 57 to assigned electronic components, for example the light source 35 or the photodectector 36. The electrical lines 81 can be obtained by means of a patterned metallization of the substrate 50. The metallization of the substrate 50 can be applied on an insulating layer and/or be covered by means of an insulator layer, in order to avoid undesirable creepage currents or short circuits. In other embodiments of the invention, the electrical lines 81 can also be obtained by introducing dopants into the substrate 50.

Furthermore, the substrate 50 can comprise an optical interface 58. The optical interface 58 can be used for coupling the light from a radiation source arranged on the second substrate 56 into the waveguide 42.

In order to improve the mechanical strength of the connection between the first substrate 50 and the second substrate 56, it can be provided that the first substrate 50 has a recess 55. The recess 55 can be shaped complementarily with respect to the outer contour of the second substrate 56. In this way, the mechanical strength of the connection between the first substrate 50 and the second substrate 56 can be increased by positively locking connection.

FIG. 5 shows a first substrate 50 having a resonance body 11 and a resonator 70 as described in association with FIG. 4.

Furthermore, FIG. 5 shows a second substrate 56. The second substrate 56 comprises the light sources 40 by means of which a photo-acoustic excitation can be performed in the resonator 70. The light sources 40 couple, by means of an optical interface 58, to the waveguide 42 running into the interior 18 of the resonator 70.

Furthermore, the second substrate 56 comprises the device 44 for controlling the light sources 40, the devices 17 and 60 for signal processing and also the device 20 comprising the solar cell 22 for the energy supply of the gas sensor 1. In this way the electronic components are substantially separated from the micromechanical components such that it is possible to combine both assemblies in a different design. By way of example, different designs of the second substrate can be provided which comprise different light sources 40 or different signal processing devices 60, in order thus to adapt the gas sensor 1 to different tasks in a simple manner by exchanging the second substrate 56. Furthermore, it can be provided that the first substrate 50 consists of a different material than the second substrate 56, such that each substrate can be optimized for the task accorded to it.

For mechanically fixing the second substrate 56, the latter engages into a recess 55 having approximately a complementary shape. In this way, the substrate 56 is mounted on the first substrate 50 in a positively locking manner. In other embodiments of the invention, the second substrate 56 can also be fixed on the first substrate 50 in a different way, for example by bonding, adhesive bonding, soldering or welding.

It goes without saying that the exemplary embodiments illustrated can be combined in order to obtain further embodiments of the invention in this way. Therefore, the above description should not be regarded as restrictive, but rather as explanatory. The description and the following claims should be understood such that a feature mentioned is present in at least one embodiment of the invention. This does not preclude the presence of further features. Insofar as the claims or the description define(s) "first" and "second" features, this designation serves to distinguish between two features of identical type, without defining an order of rank.

The invention claimed is:

1. A photo-acoustic gas sensor, comprising a resonance body and an interferometer for identification of an oscillation of the resonance body by an optical detection of a location of at least one partial area of the resonance body, wherein the interferometer is arranged on exactly one substrate of a semiconductor material, and the resonance body is formed by at least one first cutout in the substrate which at least partly separates a first elongated element of the substrate from a portion of the substrate, wherein at least one of a device for generating light, a device for detecting light, a device for electronic signal processing, or a device for energy supply is integrated on the substrate of the semiconductor material.

2. The gas sensor according to claim 1, comprising further at least one resonator which at least partly delimits a volume intended for receiving molecules to be detected.

3. The gas sensor according to claim 2, wherein the resonator is connected to the substrate by means of a bonding method and/or is monolithically integrated in the substrate.

4. The gas sensor according to claim 1, comprising at least one first substrate, comprising the resonance body and the interferometer for identifying an oscillation of the resonance body, and at least one second substrate, on which at least one device for generating light and/or a device for detecting light and/or a device for electronic signal processing and/or a device for energy supply are/is integrated on the substrate, wherein the first substrate and the second substrate is connectable by means of electrical and/or optical contact elements.

5. The gas sensor according to claim 4, wherein the first substrate has a recess provided for receiving the second substrate.

6. The gas sensor according to claim 1, wherein the resonance body has at least the first elongated element and a second elongated element, wherein the first and second elongated elements are arranged approximately parallel to each other and wherein each of these elements is fixed to a connecting element at a base point and projects freely at their end opposite to the base point, wherein a second cutout is formed between the first elongated element and the second elongated element.

7. The gas sensor according to claim 1, wherein the interferometer comprises at least two optical waveguides which are guided parallel in a partial section, such that a crosstalk of the signals respectively guided in the optical waveguides is possible.

8. The gas sensor according to claim 1, wherein at least one first electronic component is integrated on the substrate by means of CMOS technology and/or a second electronic component is connected to the substrate by means of flip-chip bonding.

9. The gas sensor according to claim 1, wherein the device, for electronic signal processing comprises a device for the radio transmission of a data signal and/or an A/D converter and/or a signal amplifier and/or a discriminator and/or a receiving device for a data signal.

10. The gas sensor according to claim 1, wherein the device for energy supply comprises at least one photovoltaic cell or a monolithically integrated photovoltaic cell.

11. The gas sensor according to claim 1, comprising further at least one contact layer adapted to electrically connect at least one of: at least two devices or at least two electronic components of a device.

12. The gas sensor according to claim 1, wherein at least one optical waveguide is integrated using silicon-on-insulator technology on and/or in the substrate.

* * * * *

UNITED STATES PATENT AND TRADEMARK OFFICE
CERTIFICATE OF CORRECTION

PATENT NO.           : 9,068,926 B2                                    Page 1 of 1
APPLICATION NO.      : 13/501779
DATED                : June 30, 2015
INVENTOR(S)          : Wolfgang Schade It is certified that error appears in the above-identified patent and that said Letters Patent is hereby corrected as shown below:

In the Claims

Claim 1, line 47, after body insert --comprising--; delete "is formed by at least one first cutout in the substrate which at least partly separates";

Line 49, after substrate delete "from"; insert --and--;

Line 50, after substrate insert --separated at least in part from the first elongated element by at least one first cutout in the substrate--.

Signed and Sealed this
Fifth Day of January, 2016

Michelle K. Lee
*Director of the United States Patent and Trademark Office*